United States Patent [19]

LeMay

[11] 4,088,887
[45] * May 9, 1978

[54] RADIOGRAPHY METHOD COMPRISING DETERMINATION OF CORRECTED ABSORPTION VALUES FOR MEMBERS OF SETS OF MUTUALLY INCLINED BEAM PATHS

[75] Inventor: Christopher Archibald Gordon LeMay, Osterley, England

[73] Assignee: EMI Limited, Hayes, England

[*] Notice: The portion of the term of this patent subsequent to Mar. 1, 1994, has been disclaimed.

[21] Appl. No.: 716,566

[22] Filed: Aug. 23, 1976

Related U.S. Application Data

[62] Division of Ser. No. 639,478, Dec. 10, 1975, Pat. No. 4,010,371.

[51] Int. Cl.² ...................... A61B 6/02; G01N 23/08
[52] U.S. Cl. ................................. 250/366; 250/369; 250/445 T
[58] Field of Search ................... 250/445 T, 360, 363, 250/366, 368, 369

[56] References Cited

U.S. PATENT DOCUMENTS

| | | | |
|---|---|---|---|
| 3,996,467 | 12/1976 | Froggatt et al. | 250/366 |
| 4,002,910 | 1/1977 | LeMay | 250/360 |
| 4,010,371 | 3/1977 | LeMay | 250/366 |

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In an X-ray apparatus for examining a body a source of a fan of radiation and detectors of the radiation along beams in the fan are traversed in a plane to provide data for a plurality of sets of parallel beams in the plane. An orbital motion is provided to give data for further sets at different inclinations in the plane. The data can be processed by arrangements using such "parallel" sets. The orbital motion is continuous during the traverse but the extent of angular change in one lateral scan is kept small so that lack of parallelism in the "parallel" sets does not give excessive errors.

3 Claims, 5 Drawing Figures

RADIOGRAPHY METHOD COMPRISING DETERMINATION OF CORRECTED ABSORPTION VALUES FOR MEMBERS OF SETS OF MUTUALLY INCLINED BEAM PATHS

This is a divisional of application Ser. No. 639,478, filed Dec. 10, 1975 and now U.S. Pat. No. 4,010,371.

This invention relates to a method of and apparatus for constructing a representation of the variation of absorption of a planar slice of a body with respect to penetrating radiation such as X- or γ- radiation.

In U.S. Pat. No. 3,778,614 methods of and apparatus for constructing such a representation are described. According to one example described in that specification, a suitable source of radiation provides a pencil beam of radiation and a suitable detector is arranged to provide a measure of the absorption suffered by the beam in passing through the body. The source and detector are each provided with a scanning movement, relative to the body, to provide such a measure of absorption for each of a plurality of substantially parallel pencil beams of radiation at each of a plurality of inclinations in the plane of the slice. Those measurements of absorption are then processed by suitable means to provide a distribution of linear absorption coefficients for the said slice. To provide the required plurality of beams the source and detector are reciprocated in the plane of the slice and orbited in steps about a common axis normal to that plane.

The processing described in the aforementioned specification is such that the finally displayed distribution of absorption coefficients is the result of successive approximations. In the complete specification of our U.S. Pat. No. 3,924,129 there is described an apparatus for processing the derived absorption data signals in which the successive approximations are made by a convolution method in which the final display of the absorption distribution can be produced more rapidly than by the procedure of the said U.S. Pat. No. 3,778,614.

In our co-pending U.S. Pat. No. 3,946,234 there is described a variation of the apparatus of the said U.S. Pat. No. 3,778,614 for the same purpose, in which a source of radiation is arranged to provide a beam of radiation which has a wide angular spread in the plane of the slice. That beam is divided into a plurality of pencil beams by suitable collimators and an array of detectors is provided to measure the intensity of each of those beams after passage through the body. Scanning motions as described hereinbefore are further imposed on the source and detectors. As a result of the reciprocating movement the array of detectors provides absorption information relating to a plurality of sets of parallel beam paths, of radiation, the sets being angularly spaced by the angular separation of the beams. Thus the orbital step between each reciprocating movement may be through a relatively larger angle. That variation of the apparatus is therefore capble of providing a faster scanning movement than that of the said U.S. Pat. No. 3,778,614. However, for the examination of certain parts of the body it is desirable to further increase the scanning rate. A substantial increase in scanning rate is however made difficult by the requirement that the orbital movement should be intermittent.

It is an object of this invention to provide a variation of the said apparatus for which a continuous orbital movement is possible.

It is another object of the invention to provide a method of examining a slice of a body by means of penetrating radiation, such an X-radiation, including the steps of: evaluating the absorption suffered by the radiation in passing through the body along a plurality of sets of mutually inclined beam paths, within the slice, each set of beam paths being orientated at a respective mean angle in said slice; determining a corrected absorption value for each beam path of each set, corrected in response to the absorption values for other beam paths of the set, and distributing said corrected values to a data store representing a notional matrix of elements in said slice, the corrected value being distributed in each case among storage locations representing elements within pre-determined distances of the respective inclined beam paths, each correction being appropriate for a notional set of parallel beam paths, having a prearranged separation of adjacent beam paths and having substantially the same distribution in at least a selected part of the said slice as the corresponding set of inclined beam paths.

In order that the invention may be clearly understood and readily carried into effect one example thereof will now be described with reference to the accompanying drawings of which:

As described hereinbefore, a requirement for a stepped orbital movement is one factor limiting the scanning rate of the aforementioned apparatus. In the arrangement of the present invention the stepped movement is replaced by a continuous orbital motion so that the required data can be obtained at an increased rate.

Figure 1:
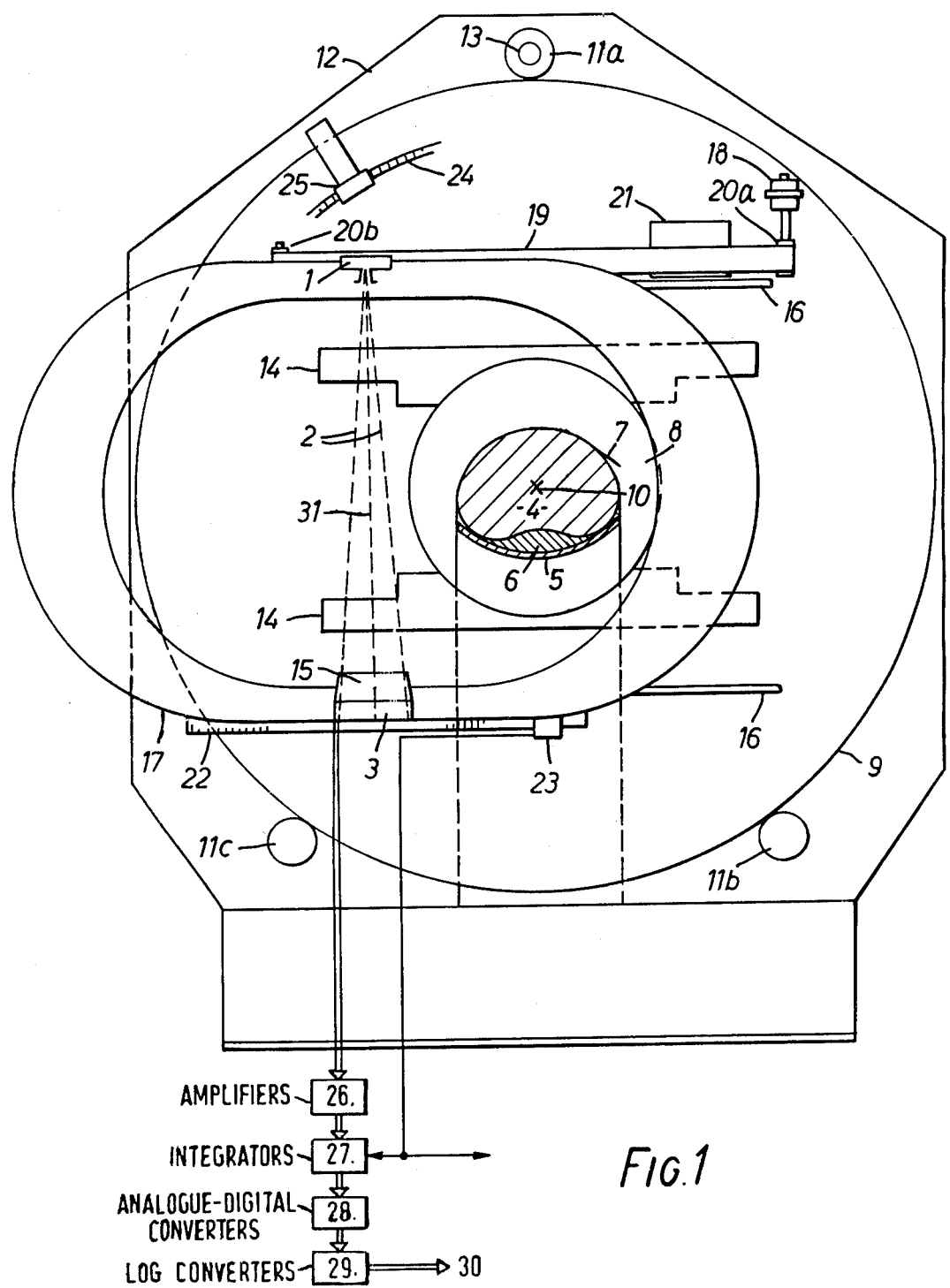
FIG. 1 shows an apparatus suitable for use with the invention.

Referring now to the drawings, FIG. 1 shows in end elevation an apparatus of the type described in the aforementioned U.S. application Ser. No. 502,080 now U.S. Pat. No. 3,946,234 adapted for use with continuous rotation according to the principles of the invention. A source 1 directs a fan shaped spread of radiation 2 towards a bank of detectors 3. The source 1 may be a rotating anode tube of known type to be as light as possible for a conventional source and the detectors 3 may be of any suitable kind such as scintillation crystals with associated photomultipliers.

A body 4, a patient to be examined, is supported on a suitably shaped bed 5. A material 6, having an absorption similar to that of body tissue is positioned between the body 4 and the bed 5 to substantially exclude air from the gap therebetween and is extended partly about the body to provide an approximately circular cross-section to examining radiation.

The body is retained firmly in a desired position by means such as a restraining strap 7. If desired more rigid means may be provided to hold the body, for example a two part rigid ring attached to bed 5.

The bed 5 and body 4 are inserted into an aperture 8 in a rotatable member 9 on which source 1 and detectors 3 are mounted. The rotatable member 9 is arranged to rotate about an axis 10 central to aperture 8 and perpendicular to the paper. For that purpose it is supported on three gear wheels 11a, b, and c which engage with teeth, not shown, cut into the periphery of member 9. The gear wheels 11 are journalled in a main frame 12 of the apparatus, which may be of any form suitable to support the rotating parts. Gear wheel 11a is driven by a motor 13 also mounted on mainframe 12.

Rotatable member 9 may also if desired carry two compensating members 14 fixed thereto. These members are arranged to provide a substantially uniform absorption to radiation traversing body 4 along a plurality of parallel beam paths, such as are to be provided by the apparatus, despite the "circular" cross section of the body and surrounding material. Thus it may be ensured that detected variations of absorption are caused substantially only by variations in the body 4. Members 14 are mounted on member 9 so that they intersect the plane of the radiation.

Associated with detectors 3 there are provided collimators 15 arranged to define a plurality of substantially equiangularly spaced beams of radiation in the fan 2. As mentioned hereinbefore a plurality of sets of parallel beam paths of the radiation through the body are to be provided. For this purpose source 1 and detectors 3, together with collimators 15 are arranged to move laterally relative to rotatable member 9. They are therefore arranged to move on bearings in respective tracks 16. In order to maintain their proper relationship the source and detectors are also joined by a lightweight but rigid yoke 17. Yoke 17 is constructed so that it foes not interfere with the passing of radiation from source 1 to detectors 3 or with fixed members 14.

Also fixedly secured to the member 9 there is a reversible motor 18 which drives a toothed belt 19 by means of a drive shaft 20a journalled in member 9. The belt 19 also passes over an idler wheel 20b on as a shaft also journalled in frame 9. The source 1 is thus subject to the required reciprocating lateral motion relative to member 9 and, by means of yoke 17, the detectors 3 also execute that motion. A counter balance weight 21 is fixed to belt 19 opposite to source 1 to compensate for out of balance forces during the lateral movement. The relative motions are such that, in this example 2.9° of rotation occur in the time of one lateral scan.

Also carried by yoke 17 there is a graticule 22 which is a translucent strip carrying engraved lines which interrupt light passing between a light source and photocell 23 fixed to member 9. The signals obtained in response to the interruption are used by a computer controlling the processing to determine the positions of the source and detectors relative to the member 9 for respective data values obtained by the detectors. A similar graticule 24, shown in part, is in the form of a ring fixed to member 9. This cooperates in similar manner with a photocell and light source 25, fixed to mainframe 12 to provide information relating to the progress of the orbital motion for the same purpose.

The arrangement is such that, as source 1 and detectors 3 are scanned laterally each detector provides an output signal indicative of the radiation incident thereon. These signals are amplified in a respective one of amplifiers 26 and integrated in a respective one of integrators 27 for an integration period determined by pulses from photocell 23. The signal thus provided by each integrator in one period represents a datum for a beam path incident on the respective detector and of width defined by the extent of the lateral motion in the integration period. The data are converted to digital form in converters 28 and to logarithmic form in converters 29 for provision at 30 to further processing which will be discussed hereinafter.

The apparatus so far described is, except in two respects, essentially the same as that disclosed in the said U.S. Pat. No. 3,946,234. The two differences are that motor 13 is arranged to provide a steady rotation of member 9, and the equipment mounted thereon, instead of an intermittent motion and that the angle through which the apparatus rotates in the course of one lateral scan is relatively less than the angular step of the previous arrangement. The rotation is normally of such an extent that the body is irradiated over a total angle of 180° but may be greater than that if desired.

Figure 2:
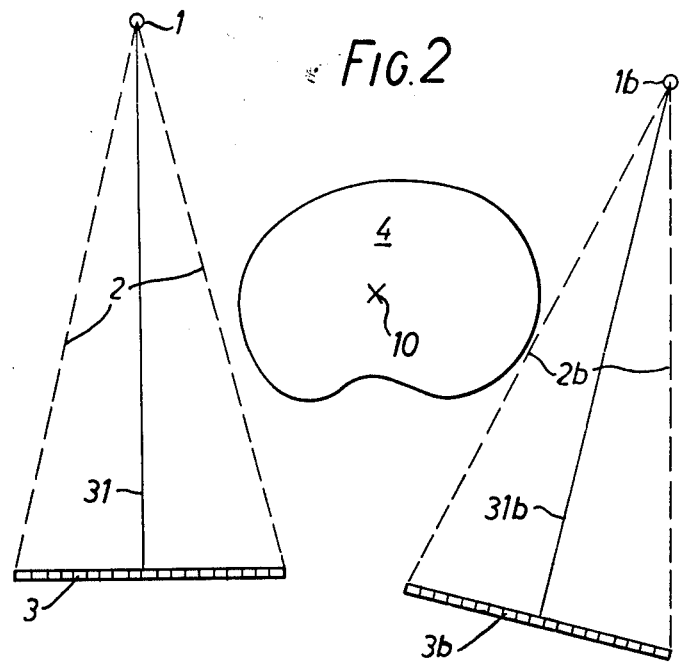
FIG. 2 illustrates the scanning motion employed.

FIG. 2 shows the scanning arrangement in simplified form for the purpose of illustrating the motions involved. The source 1 of radiation provides the fan shaped spread of radiation indicated as before by the broken lines 2. It should be noted that, although the array of detectors is shown in straight line, the detectors may be arranged in arc, if desired, to be equidistant from source 1.

As mentioned hereinbefore it is desired that each pencil beam of fan 2, typified by central beam 31, provides, in effect, data for a set of parallel beam paths. In the apparatus of the said U.S. application Ser. No. 502,080 now U.S. Pat. No. 3,946,234 procedure is repeated at a plurality of orbital positions. For apparatus using the said convolution processing data for each such parallel set is processed to give, for each beam path position in the set, a corrected value of absorption taking into account the values for other beam path positions. These corrected values are calculated so that, considering a small element of the planar slice of the body, the absorption coefficient for that element may be obtained with sufficient accuracy by suitable combination of the corrected values for all beam paths passing through that element. In practice it is desirable that the beam paths pass through the centres of the chosen elements of the slice and interpolation is employed to take account of the fact that beams do not, in general, fulfil this desideratum.

In the arrangement of the present invention the continuous movement and a single lateral movement combined take the source to a position such as that shown in FIG. 2 at 1b. For that position the beam limits, detector array and centre beam are indicated by 2b, 3b and 31b respectively. It will be seen that in the course of one lateral movement the centre beam will have provided in effect a set of beam paths, across body 4, substantially equally spaced at a plurality of angular positions. For the preferred embodiment of the invention, which employs a fan of 30 beams of ⅓° spacing, the scanning arrangement is designed so that each beam turns through an angle of 2.9°, in the course of a lateral scan, rather than 10° as in the previous arrangement.

It will be apparent that the set of beam paths thus provided for each beam of the fan does not represent a parallel set as assumed for the said convolution processing. However it has been found that, if the total deviation from parallelism over the entire beam path set is restricted to the order of 3°, the convolution processing may be employed without significant error. The explanation for this is found in the nature of the convolution processing. Each path value, that is each signal representing the transmission of radiation along the respective beam paths, is ammended by the addition of a term for each other beam path in the set. Each of those terms is moreover provided by multiplying the value for the respective beam path with a factor related to the position of that beam path in the set relative to the beam path being corrected. Thus the correction terms for a beam path tend to be in inverse importance to the distance of the beam path providing them. The relevance of this can be seen in relation to FIG. 3 which shows a set of only seven beam paths at an exaggerated angular spacing. The beam paths are labelled 32 to 38. If the convolution processing is to be applied to the absorption value for beam path 35 the maximum factors will be for beam paths 34 and 36, intermediate values for beam paths 33 and 37 and minimum for beams paths 32 and 38. However it is beam paths 32 and 38 which deviate from parallelism with beam path 35 and beam paths 34 and 36 which deviate least. Therefore, in terms of the processing, the error resulting from lack of parallelism is reduced by the low weighting of the most extreme values.

It is therefore arranged to apply convolution processing to the beam paths of each such set as if they were parallel to provide the required corrected values of beam path signals. If the slice is now divided into a notional matrix of element it is necessary to put into a location of the processing store for each element the corrected values for the beam path of the set which pass sufficiently near to the centre of that element. To ensure that one such beam path exists for every set, interpolation, such as that described in our co-pending U.S. application Ser. No. 596,623 is provided to give, for example, 40 values between each pair of beam paths. Each value is stored at its appropriate position and allocated to those elements of the slice which are expected to be intersected by that beam path.

Although, for the example described hereinbefore in which the angular spread is small, the lack of parallelism of the beam paths does not significantly affect the convolution factors in general it is true that the factors should be different for different spacings of beam paths. Since, in a fan wise distribution, such spacings vary, the factors chosen for, say, the spacing as at the centre of the body will be in error for elements nearer to or further from the source. if the orbital scan is continued through 360°, so that identical beam path provide two absorption values irradiated in opposite directions, there is an opposite effect and residual errors are small. Otherwise, since the error can be calculated in advance for a known geometry, correction factors may be applied during computation.

It will be understood that the motion of the source and detectors is determined by predetermined factors such as the geometry of the apparatus. Thus for any scan it will be known as a design factor what beam paths, through aperture 8, the radiation will follow. Thus the computer controlling the processing may be provided with the required information to properly allocate the data acquired to their positions in the matrix. Although variations may be provided in the scanning motion, such variations may also be programmed in advance into the computer. Nevertheless, for the purposes of better understanding of the invention a method for properly allocating the data, as derived, will be described.

Figure 4:
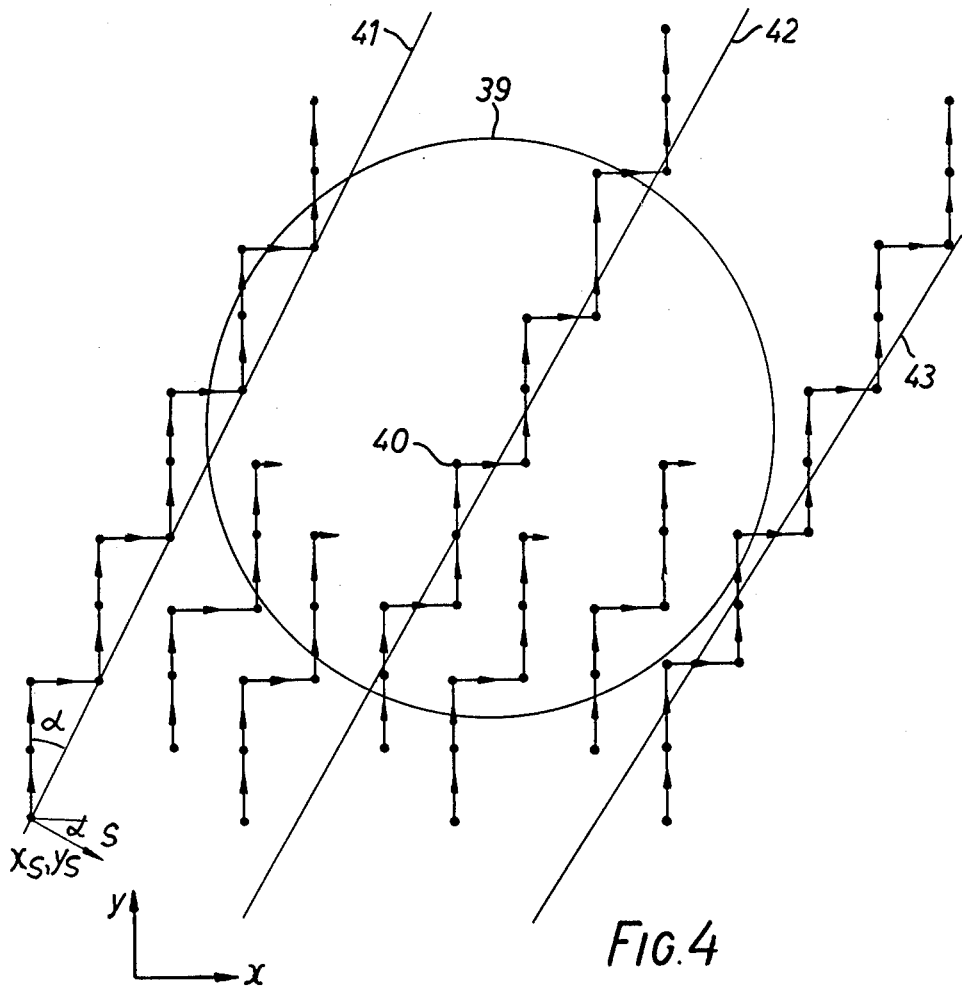
FIG. 4 illustrates a method of organising the data obtained.

To determine which beam path of the enlarged set, i.e. the set including the forty interpolated beam values between each two real beam values should pass through any element a method using a set of 'pseudo-beams' will be described. These pseudo-beams are arranged to cross the matrix of elements in zig-zag paths, intersecting elements centre points, such that they approximately follow the path of the actual and interpolated beam paths. This is illustrated in FIG. 4 for a typical cartesian matrix of elements of a slice. For clarity the slice is shown to have a much reduced number of such elements than the practical embodiments. In FIG. 4 the region of interest is indicated by the circle 39. This has superimposed on it a matrix of elements, some of which are indicated by their centre points, such as 40. Seven pseudo beams are shown, only three in full. The beams are of equal length and are arranged so that together they intersect every element in the region of interest. Three of the real non-parallel, beam paths of the set are indicated by lines 41, 42 and 43. It can be seen that the psuedo beams follow the general direction of the three beam paths shown. The other real beam paths of the set, together with the interpolated beam paths, have not been shown in FIG. 4 for the sake of clarity. The movements of the psuedo-beams from one element to the next are parallel to arbitrary axes $x$ and $y$, the number of $y$ steps in succession being $\Delta y$ and the number of $x$ steps in succession being $\Delta x$. Each pseudo-beam is formed of a total of D, $x$ or $y$ steps. For the pseudo-beams shown in FIG. 4 $\Delta y = 2$, $\Delta x = 1$ and D = 14. Each pseudo beam is characterised by particular values of $\Delta y$, $\Delta x$ and D.

The pseudo beams are used to determine the beam path of the interpolated set which passes closest to the centre of any particular element The numbers of each beam path are functions of its distance along, that is position in, the set. A particular value of S is chosen to distinguish the required beam path. The value of S is set for the starting point $x_S$, $y_S$, of the first pseudo beam which corresponds to one of the real beam paths of the set, and is updated for each step of the psueudo-beam. If the real beam path at the starting point makes an angle $\alpha$ with the y-axis the parameters $\Delta x$ and $\Delta y$ are set to give $\Delta x/\Delta y = \tan \alpha$ and the corrections for S, to determine the number of the real or interpolated beam which passes through, or sufficiently close to, the centre of each element in turn along the pseudo beam, are $\delta s/\delta x = \cos \alpha$ and $\delta s/\delta y$ 32 $\sin \alpha$, where $\delta x$ and $\delta y$ are the increments in $x$ and $y$ from the last point reached by the last correction in S. S can therefore be updated by the value of $\delta s/\delta y$ or $\delta s/\delta y$ or $\delta s/\delta x$ appropriate to the step being considered for each movement of the zig-zag pseudo-beam about the line of the real beam path. However, although the values of $\Delta x$ and $\Delta y$ are set so that the pseudo-beams follow the first real beam path of the set, that is hence the same mean direction, the other real beam paths for the same set will deviate from the nearest pseudo-beam if they are characterised by the same values of $\Delta x$ and $\Delta y$. If this is not corrected at the ends of all but the first pseudo-beam there will be a deviation from the correct value of S for the real beam path that is the choice of interpolated beam will tend to be incorrect. A correction is made for this as follows. If the real beam path at the end of the pseudo-beam is inclined to the $y$ axis at angle $\alpha f$, the change in S over the length of the pseudo-beam is N $\sin (\alpha - \alpha f)$ where N is the number of elements in the $x$ direction, equal to the number of beam path spaces, over which the pseudo-beam extends. Thus if the change in S is distributed equally over all of the steps of the pseudo-beam a correction C = N $\sin (\alpha - \alpha f)/D$ is obtained. Thus the total correction for each step is $(\delta s/\delta x) + C$ or $(\delta y/\delta s) + C$ for an $x$ step or a $y$ step respectively. As an alternative, corrections could be made to the values of $\Delta x$ and $\Delta y$ for each pseudo-beam.

In operation Δx and Δy are calculated, for the start of the first pseudo-beam for one beam path set, and δs/δx, δs/δy and C evaluated. It will be appreciated that C will have a value of zero for the first pseudo-beam. As the pseudo-beam is followed values of absorption are obtained, from the stored set of absorption values after interpolation, for each element of the matrix in response to the value of S calculated. These are added to the already stored absorption values for the respective elements. After D steps the next pseudo-beam is commenced using the same values of Δx and Δy but with a new value for C. After this procedure has been completed for every beam path, of every such set of beam paths in the complete orbital movement, the absorption values, stored in each element of the matrix, give the required representation of absorption for the slice.

As described the values of Δx and Δy are set for the first real beam path of the set so that C has a value of zero for the associated pseudo-beam. However it will be appreciated that Δx and Δy could be set for any of the real beam paths. If they are determined for a real beam path in the middle of the set the deviation determining C can be distributed substantially equally about a centre value of zero.

The arrangement described uses forty interpolated absorption values for each pair of real beam paths of a set. The storage required to retain these values may be reduced by interpolating and then generating pseudo-beams for only, say, seven real beam paths at one time. The stored interpolated values would then be reduced in number to, in the present example, 280 values.

It will be appreciated that other systems may be employed for allocating the interpolated absorption values to their respective elements of the matrix.

Figure 3:
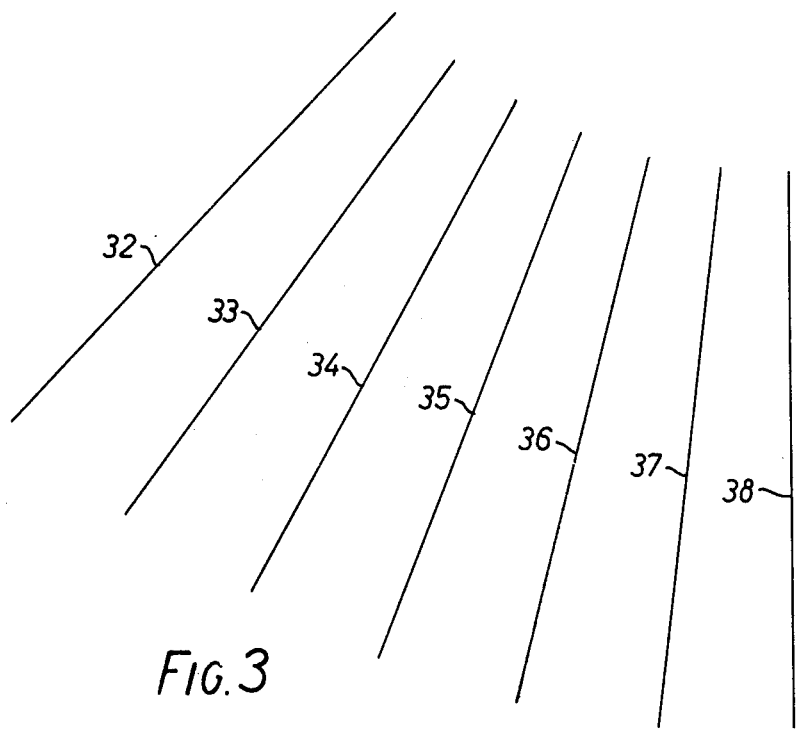
FIG. 3 is used to explain the principle of the invention.
Figure 5:
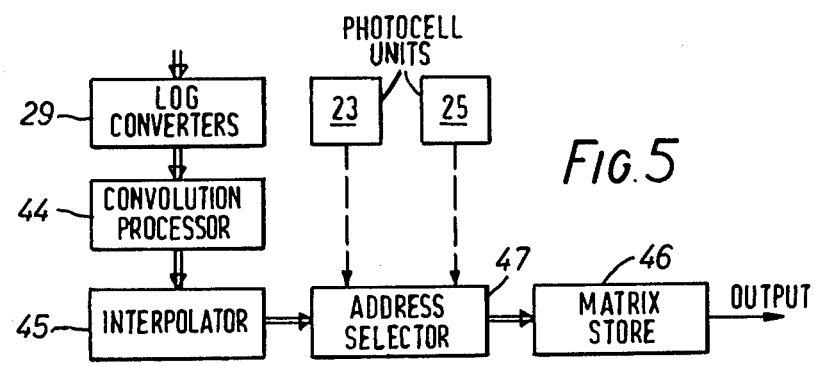
FIG. 5 shows in block diagrammatic form a processing arrangement for the invention.

FIG. 5 shows, in simplified block diagrammatic form, the organisation of data processing for the invention following log conversion in converters 29 as described in relation to FIG. 1. The digital data are first provided to a processing computer 44 where they are processed to provide data suitable for adding directly to the final matrix at the correct locations. As mentioned hereinbefore this may conveniently be by the convolution method described in our U.S. Pat. No. 3,924,129. The data are then in the form of corrected absorption values for individual beam paths, of each set of beam paths as shown in FIG. 3. In accordance with the principles of the invention the processing is carried out as if these beams were in fact parallel.

The corrected values are then transferred to an interpolater 45 where they are pressed, for example as described in the said U.S. application Ser. No. 596,623 to provide data for, say, 40 interpolated beam paths equiangularly spaced between each pair of FIG. 3.

A computer comprising interpolator 45, or an additional computer, may also apply corrections for the relative spacing of the beams at the respective distance from the source. This may be by multiplying each entry in the matrix for a modified beam path through an element by a factor $k/d$ where $k$ is a constant and $d$ is the distance of that element from the X-ray source for the source position originating that beam path.

The interpolated and possibly corrected data are then to be stored in a matrix store 46 equally at locations representing matrix elements through which or near to which the beam paths lie. This is achieved by an address selector 47 which provides the correct addresses for each data signal in a predetermined sequence in view of the known geometry of the apparatus. Alternatively, as described hereinbefore, the addresses may be allocated in response to data from photocell units 23 and 25, via the connections shown as broken lines.

It will be understood that, although they have been shown as individual blocks, the functions of units 44 to 47 may be provided by a single digital computer.

The data from matrix store 46 are output to any suitable display arrangement for viewing as desired.

What I claim is:

1. A method of examining a slice of a body by means of penetrating radiation, such as X-radiation, including the steps of: evaluating the absorption suffered by the radiation in passing through the body along a plurality of sets of mutually inclined beam paths, within the slice, each set of beam paths being oriented at a respective means angle in said slice; determining a corrected absorption value for each beam path of each set, corrected in response to the absorption values for other beam paths of the set, and distributing said corrected values to a data store representing a notional matrix of elements in the said slice, the corrected value being distributed in each case among storage locations representing elements within predetermined distances of the respective inclined beam paths, each correction being appropriate for a notional set of parallel beam paths, having a prearranged separation of adjacent beam paths and having substantially the same distribution in at least a selected part of the said slice as the corresponding set of inclined beam paths.

2. A method according to claim 1 wherein the absorption value for each beam path in each set is corrected by the combination therewith of the absorption values for other beam paths of the set multiplied by respective factors which are related to the positions of corresponding beam paths, in the notional set of parallel beam paths, relative to the beam path corresponding to that for which the value is being corrected.

3. A method according to claim 1 wherein the angular distribution of the said sets of mutually inclined beam paths in the said slice is sufficient to irradiate the slice at each mean angle by radiation diverging in opposite directions to substantially cancel errors, in the said corrected values, related to the distances of the elements from the origin of the radiation along paths therethrough.

* * * * *